(12) United States Patent
Shigenobu et al.

(10) Patent No.: US 7,166,476 B2
(45) Date of Patent: Jan. 23, 2007

(54) HIGHLY REPRODUCIBLE AGGLUTINATION IMMUNOASSAY METHOD AND REAGENTS

(75) Inventors: Kayoko Shigenobu, Sunto-gun (JP); Kenshiro Shuto, Tsukuba (JP); Shujiro Sakaki, Tsukuba (JP)

(73) Assignees: Kyowa Medex Co., Ltd., Tokyo (JP); NOF Corporation, Tokyo (JP)

( * ) Notice: Subject to any disclaimer, the term of this patent is extended or adjusted under 35 U.S.C. 154(b) by 640 days.

(21) Appl. No.: 10/363,038

(22) PCT Filed: Aug. 28, 2001

(86) PCT No.: PCT/JP01/07385

§ 371 (c)(1),
(2), (4) Date: Feb. 28, 2003

(87) PCT Pub. No.: WO02/18953

PCT Pub. Date: Mar. 7, 2002

(65) Prior Publication Data

US 2003/0166302 A1    Sep. 4, 2003

(30) Foreign Application Priority Data

Aug. 29, 2000  (JP) .............................. 2000-259964

(51) Int. Cl.
| | |
|---|---|
| G01N 33/536 | (2006.01) |
| G01N 33/546 | (2006.01) |
| G01N 33/53 | (2006.01) |
| G01N 33/539 | (2006.01) |
| C08F 130/02 | (2006.01) |
| C07F 9/09 | (2006.01) |

(52) U.S. Cl. ...................... 436/536; 436/533; 436/539; 435/7.1; 435/961; 435/810; 526/276; 564/293

(58) Field of Classification Search ................ 436/533, 436/536, 539; 526/276; 564/293; 435/7.1, 435/961, 810

See application file for complete search history.

(56) References Cited

U.S. PATENT DOCUMENTS 5,977,257 A * 11/1999 Waki et al. .................. 525/131

FOREIGN PATENT DOCUMENTS

| EP | 0 767 212 A | 4/1997 |
|---|---|---|
| JP | 54-6325 B1 | 1/1979 |
| JP | 58-11575 A | 1/1983 |
| JP | 58-154591 A | 9/1983 |
| JP | 61-274261 A | 12/1986 |
| JP | 62-218865 A | 10/1987 |
| JP | 07 035752 A | 2/1995 |
| JP | 7-035752 A | 7/1995 |
| JP | 8-101196 A | 4/1996 |
| JP | 10 045794 A | 2/1998 |
| JP | 10 114800 | 5/1998 |

OTHER PUBLICATIONS

Gella et al Latex agglutination procedures in imunodiagnosis. 1991, Pure & Appl. Chem., vol. 63, No. 8, pp. 1131-1134.*
"Continuous cultures of fused cells secreting antibody of predefined specificity", Nature vol. 256, pp. 495-497, Aug. 7, 1975.
Sakaki, S. et al., "Stabilization of an Antibody Conjugated with Enzyme by 2-Methacryloyloxyethyl Phosphorylcholine Copolymer In Enzyme-Linked Immunosorbent Assay", Journal of Biomedical Materials Research, Wiley, NY, vol. 47, No. 4, 1999, pp. 523-528.
Martin, L.M., "Facile Reduction in the Synthesis of Phosphorylcholine Affinity Columns", Tetrahedron Letters, Elsevier, Amsterdam, NL, vol. 37, No. 44, Oct. 28, 1966, pp. 7921-7924.
Ishihara, K. et al., "Why do Phospholipid Polymers Reduce Protein Adsorption?", Journal of Biomedical Materials Research, Feb. 1998, vol. 39, No. 2, Feb. 1988, pp. 323-330.
Clarke, S. et al., "Novel Biomimetic Polymers Incorporating Phosphorylcholine",, Journal of Pharmacy and Pharmacology, vol. 52, No. Supplement, Sep. 2000, p. 114.

* cited by examiner

*Primary Examiner*—Long V. Le
*Assistant Examiner*—Shafiqul Haq
(74) *Attorney, Agent, or Firm*—Ann S. Hobbs; Robert Kinberg; Venable LLP

(57) ABSTRACT

The present invention provides an agglutination immunoassay, wherein the agglutination of insoluble carrier particles such as latex are stabilized and uniformized to give good reproducibility, and a reagent therefor. In the agglutination immunoassay which comprises allowing an antigenic substance in a sample to bind to insoluble carrier particles carrying substantially neither antigens nor antibodies thereon, and allowing an antibody or an antibody complex which reacts specifically to the antigenic substance to bind to the antigenic substance to give a selective agglutination of the insoluble carrier particles, a homopolymer prepared by polymerization of a monomer such as 2-methacryloyloxyethyl phosphorylcholine having a phosphorylcholine group and a vinyl group, or a copolymer prepared by polymerization of a monomer having a phosphorylcholine group and a vinyl group, with a monomer having a vinyl group such as n-butyl methacrylate is used.

23 Claims, No Drawings

HIGHLY REPRODUCIBLE AGGLUTINATION IMMUNOASSAY METHOD AND REAGENTS

TECHNICAL FIELD

The present invention relates to an agglutination immunoassay, wherein an antigenic substance in an aqueous medium such as a living sample is determined immunologically by an agglutination reaction, and a reagent therefor.

BACKGROUND ART

Recently, automation of various examination such as laboratory tests and reduction of time for determination are attempted in hospitals, inspection institutions and the like in the light of shortage of manpower, cost reduction, a large quantity of samples to be treated, and the like. As a method suitable for such automation, attentions are drawn to an agglutination immunoassay, wherein an antigenic substance is determined by an agglutination reaction of insoluble carrier particles. For example, Japanese Published Unexamined Patent Application No. 35752/95 discloses an agglutination immunoassay which comprises allowing an antigenic substance in a sample to bind to insoluble carrier particles carrying substantially neither antigens nor antibodies thereon, and allowing an antibody or an antibody complex which reacts specifically to the antigenic substance to bind to the antigenic substance to give a selective agglutination of the insoluble carrier particles.

However, in an agglutination immunoassay, it is difficult to have a reaction with good reproducibility due to the non-uniformity of agglutination in an agglutination reaction of the insoluble carrier particles with antigens or antibodies. Specifically, in an agglutination immunoassay which comprises allowing an antigenic substance in a sample to bind to insoluble carrier particles carrying substantially neither antigens nor antibodies thereon, and allowing an antibody or an antibody complex which reacts specifically to the antigenic substance to bind to the antigenic substance to give a selective agglutination of the insoluble carrier particles, there are problems such as direct binding of antibodies to the insoluble carrier particles. Therefore, improvement of reproducibility in the agglutination immunoassay is required.

An object of the present invention is to provide: an agglutination immunoassay which comprises allowing an antigenic substance in a sample to bind to insoluble carrier particles carrying substantially neither antigens nor antibodies thereon, and allowing an antibody or an antibody complex which reacts specifically to the antigenic substance to bind to the antigenic substance to give a selective agglutination of the insoluble carrier particles due to stabilization and uniformization of an agglutination as well as prevention of non-specific adsorption; and a reagent therefor.

DISCLOSURE OF THE INVENTION

The present inventors have made a keen study to solve the above-mentioned problem and have found out that in an agglutination immunoassay which comprises allowing an antigenic substance in a sample to bind to insoluble carrier particles carrying substantially neither antigens nor antibodies thereon, and allowing an antibody or an antibody complex which reacts specifically to the antigenic substance to bind to the antigenic substance to give a selective agglutination of the insoluble carrier particles, a compound having a group analogous to a phosphorylcholine group has an action to promote and uniformize the agglutination of the carrier particles by an antigen-antibody reaction to give a stable and uniform agglutination as well as improvement in reproducibility. The present invention has been thus completed.

The present invention relates to an agglutination immunoassay which comprises allowing an antigenic substance in a sample to bind to insoluble carrier particles carrying substantially neither antigens nor antibodies thereon, and allowing an antibody or an antibody complex which reacts specifically to the antigenic substance to bind to the antigenic substance to give a selective agglutination of the insoluble carrier particles, wherein a compound having a group represented by formula (I) (wherein n is an integer of 1 to 6, and $R^1$, $R^2$ and $R^3$ are the same or different, and independently represent hydrogen, substituted or unsubstituted alkyl having 1 to 6 carbon atoms) is used (claim 1); the agglutination immunoassay according to claim 1, wherein the compound having a group represented by formula (I) is a compound prepared by polymerization of a monomer having a group represented by formula (I) (claim 2); the agglutination immunoassay according to claim 1, wherein the compound having a group represented by formula (I) is a compound prepared by polymerization of a monomer having a group represented by formula (I) with other monomer polymerizable with the monomer having a group represented by formula (I) (claim 3); the agglutination immunoassay according to claim 3, wherein the other monomer polymerizable with the monomer having a group represented by formula (I) is a monomer having a vinyl group (claim 4); the agglutination immunoassay according to claim 4, wherein the monomer having a vinyl group is n-butyl methacrylate (claim 5); the agglutination immunoassay according to any of claims 2 to 5, wherein the monomer having a group represented by formula (I) is a monomer having a group represented by formula (I) and a vinyl group (claim 6); the agglutination immunoassay according to any of claims 1 to 6, wherein the group represented by formula (I) is a phosphorylcholine group (claim 7); the agglutination immunoassay according to claim 6, wherein the monomer having a group represented by formula (I) and a vinyl group is 2-methacryloyloxyethyl phosphorylcholine (claim 8); the agglutination immunoassay according to any of claims 1 to 8, wherein the antibody is an anti-hemoglobin A1c monoclonal antibody (claim 9); the agglutination immunoassay according to any of claims 1 to 9, wherein the antibody complex comprises an antibody which reacts specifically to the antigenic substance, and a secondary antibody which reacts selectively to the antibody which reacts specifically to the antigenic substance (claim 10); and the agglutination immunoassay according to any of claims 1 to 10, wherein the insoluble carrier particles are polystyrene latex (claim 11).

(Chemical formula 1)

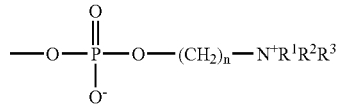

Furthermore, the present invention relates to a reagent for an immunoassay comprising a compound having a group represented by formula (I) (wherein n is an integer of 1 to 6, and $R^1$, $R^2$ and $R^3$ are the same or different, and independently represent hydrogen, substituted or unsubsituted alkyl having 1 to 6 carbon atoms) used in an agglutination immunoassay which comprises allowing an antigenic substance in a sample to bind to insoluble carrier particles carrying substantially neither antigens nor antibodies thereon, and allowing an antibody or an antibody complex which reacts specifically to the antigenic substance to bind to the antigenic substance to give a selective agglutination of the insoluble carrier particles (claim 12); the reagent for an immunoassay according to claim 12, wherein the compound having a group represented by formula (I) is a compound prepared by polymerization of a monomer having a group represented by formula (I) (claim 13); the reagent for an immunoassay according to claim 12, wherein the compound having a group represented by formula (I) is a compound prepared by polymerization of a monomer having a group represented by formula (I) with other monomer polymerizable with the monomer having a group represented by formula (I) (claim 14); the reagent for an immunoassay according to claim 14, wherein the other monomer polymerizable with the monomer having a group represented by formula (I) is a monomer having a vinyl group (claim 15); the reagent for an immunoassay according to claim 15, wherein the monomer having a vinyl group is n-butyl methacrylate (claim 16); the reagent for an immunoassay according to any of claims 13 to 16, wherein the monomer having a group represented by formula (I) is a monomer having a group represented by formula (I) and a vinyl group (claim 17); the reagent for an immunoassay according to any of claims 12 to 17, wherein the group represented by formula (I) is a phosphorylcholine group (claim 18); the reagent for an immunoassay according to claim 17, wherein the monomer having a group represented by formula (I) and a vinyl group is 2-methacryloyloxyehtyl phosphorylcholine (claim 19); the reagent for an immunoassay according to any of claims 12 to 19, wherein the antibody is an anti-hemoglobin A1c monoclonal antibody (claim 20); the reagent for an immunoassay according to any of claims 12 to 20, wherein the antibody complex comprises an antibody which reacts specifically to the antigenic substance, and a secondary antibody which reacts selectively to the antibody which reacts specifically to the antigenic substance (claim 21); and the reagent for an immunoassay according to any of claims 12 to 21, wherein the insoluble carrier particles are polystyrene latex (claim 22).

(Chemical formula 2)

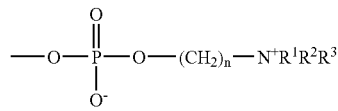

BEST MODE FOR CARRYING OUT THE INVENTION

There is no specific limitation to an agglutination immunoassay according to the present invention as long as the agglutination immunoassay is an immunoassay which comprises allowing an antigenic substance in a sample to bind to insoluble carrier particles carrying substantially neither antigens nor antibodies thereon, and allowing an antibody or an antibody complex which reacts specifically to the antigenic substance to bind to the antigenic substance to give a selective agglutination of the insoluble carrier particles, wherein a compound having a group represented by formula (I), shown below, wherein n is an integer of 1 to 6, and $R^1$, $R^2$ and $R^3$ are the same or different, and independently represent hydrogen, substituted or unsubsititued alkyl having 1 to 6 carbon atoms, is used. Further, there is no specific limitation to a reagent for an immunoassay according to the present invention as long as the reagent comprises a compound having a group analogous to a phosphorylcholine group represented by formula (I), and is used in an agglutination immunoassay which comprises allowing an antigenic substance in a sample to bind to insoluble carrier particles carrying substantially neither antigens nor antibodies thereon, and allowing an antibody or an antibody complex which reacts specifically to the antigenic substance to bind to the antigenic substance to give a selective agglutination of the insoluble carrier particles. The binding herein refers to both physical adsorption and chemical bond.

(Chemical formula 3)

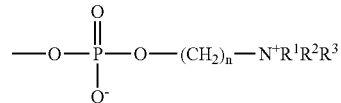

There is no specific limitation to insoluble carrier particle for the present invention as long as the insoluble carrier particles carrying substantially neither antigens nor antibodies thereon are capable of binding an antigenic substance in a sample. The examples include the known microparticles of an organic polymer described in Japanese Published Examined Patent Application No. 11575/83, microparticles of inorganic oxides or microparticles wherein the surface of these substances that are to form the core is treated with an organic substance or the like. The specific examples are synthetic resin (latex) such as polystyrene, polyvinylchloride, polypropylene, (meth)acrylic resin and poly(methyl methacrylate); cellulose derivatives such as nitrocellulose, cellulose and methylcellulose; and inorganic substances such as metal, ceramics, glass and silicon rubber. Among these substances, a polystyrene synthetic polymer, particularly a polystyrene synthetic polymer co-polymerized with an acrylate monomer or a monomer having sulfonic acid as a component to provide electric charges is preferable.

As described above, latex particles, in particular, such as polystyrene latex are preferably used in the present invention as insoluble carrier particles. Proteins and peptides can smoothly be adsorbed on latex having a surface of high hydrophobicity, such as polystyrene latex. In addition, polystyrene particles prepared by a soap-free polymerization, may preferably be used particularly, because they can remain stable without surfactants due to the repulsion raised between negative charges on the surface. Alternatively, various kinds of denatured latex (for example, denatured carboxylic acid latex), magnetic latex (latex containing magnetic particles) and the like may also be used, if necessary.

As to insoluble carrier particles, equality of the size, regulation of the surface condition, selection of the internal structure and so on are usually required at a high level for conducting quantitative immunoassay, and insoluble carrier particles such as latex favorable for the preparation of the reagents can be selected from those commercially available.

A shape of insoluble carrier particles is not particularly limited, and a sphere shape is exemplified. As a particle diameter in sphere-shaped particles, for instance, 0.03 to 0.8 µm on average is preferable, and 0.06 to 0.2 µm on average is more preferable. In the present invention, there is no specific limitation to a concentration of insoluble carrier particles in a reaction solution, and the concentration is, for example, 0.001 to 10% by weight, preferably 0.005 to 5% by weight and more preferably 0.01 to 2% by weight to stabilize and uniformize the agglutination reaction of insoluble carrier particles more.

As a compound having a group represented by formula (I) in the present invention, there is no specific limitation as long as the compound is a compound having a group represented by formula (I) wherein n is an integer of 1 to 6, and $R^1$, $R^2$ and $R^3$ may be the same or different, and independently represent hydrogen, substituted or unsubstituted alkyl having 1 to 6 carbon atoms. Examples of alkyl part of $R^1$, $R^2$ and $R^3$ in formula (I) include methyl, ethyl, propyl, butyl, isobutyl, pentyl, hexyl and the like. Moreover, number of substituents in the substituted alkyl is 1 to 3, and examples of the substituent include hydroxy, aryl and the like. Examples of the aryl include benzyl, naphthyl and the like.

In addition, examples of the compound having a group represented by formula (I) include a compound prepared by polymerization of a monomer having a group represented by formula (I), a compound prepared by copolymerization of a monomer having a group represented by formula (I) with other monomer polymerizable with the monomer having a group represented by formula (I), and the like. As the monomer having a group represented by formula (I), a monomer having a group represented by formula (I) and a vinyl group is preferably exemplified. Furthermore, as other monomer polymerizable with the monomer having a group represented by formula (I), a monomer having a vinyl group is preferably exemplified.

As a group represented by formula (I) in the present invention, a phosphorylcholine group (hereinafter abbreviated as PC group) is preferably exemplified. Therefore, as a compound having a group represented by formula (I) in this present invention, a compound having PC group is preferably exemplified. In addtion, there is no specific limitation to a compound having PC group. As a compound having a PC group, a polymer prepared by polymerization of a monomer having a PC group, and a polymer prepared by copolymerization of a monomer having a PC group with other monomer polymerizable with the monomer having a PC group are preferably exemplified. Among the compound having a PC group, a polymer prepared by polymerization of a monomer having a PC group and a vinyl group, and a polymer prepared by copolymerization of a monomer having a PC group and a vinyl group with other monomer polymerizable with the monomer having a PC group and a vinyl group are more preferably exemplified.

There is no specific limitation to a monomer having a PC group and a vinyl group. Examples of the monomer having a PC group and a vinyl group include 2-acryloyloxyethyl phosphorylcholine, 2-methacryloyloxyethyl phosphorylcholine (abbreviated hereinafter as MPC), 2-(meth)acryloyloxyethoxyethyl phosphorylcholine, 6-(meth)acryloyloxyhexyl phosphorylcholine, 10-(meth)acryloyloxyethoxynonyl phosphorylcholine, allyl phosphorylcholine, butenyl phosphorylcholine, hexenyl phosphorylcholine, octenyl phosphorylcholine, decenyl phosphorylcholine, and the like. In addition, these monomers can be prepared according to the known methods described in Japanese Published Unexamined Patent Application No. 6325/79, Japanese Published Unexamined Patent Application No. 154591/83, and the like.

Other monomers polymerizable with the monomer having a PC group, preferably the monomers having a vinyl group include a (meth)acrylate such as methyl (meth)acrylate, ethyl (meth)acrylate, n-butyl (meth)acrylate, isobutyl (meth)acrylate, pentyl (meth)acrylate, hexyl (meth)acrylate, heptyl (meth)acrylate, octyl (meth)acrylate, tridecyl (meth)acrylate, 2-hydroxyethyl methacrylate; a styrene monomer such as styrene, α-methyl styrene, styrene having a phenyl group substituted with methyl group(s) and styrene having a phenyl group substituted with chlorine atom(s); a substituted or unsubstituted hydrocarbon monomer such as vinyl chloride, vinylidene chloride, ethylene, propylene and isobutylene; a vinylester monomer such as vinyl acetate and vinyl propionate; a vinyl ether monomer such as ethyl vinyl ether and n-butyl vinyl ether; diethyl itaconate, di(n-butyl) itaconate, and the like. Among these monomers, esters of methacrylic acid (methacrylate), styrene and the like are preferable, and n-butyl methacrylate (abbreviated hereinafter as BMA) is particularly preferable.

A polymer comprising a PC group can be prepared by a conventional polymerization method such as radical polymerization, wherein components for polymerization comprising the above-mentioned monomer having a PC group are polymerized in the presence of a polymerization initiator. As a polymerization initiator, there is no specific limitation as long as the initiator is an initiator usually used for radical polymerization, and the following are preferably exemplified: 2,2'-azobis(2-methyl propionamidine) dihydrochloride, 4,4'-azobis(4-cyanovaleric acid), 2,2'-azobis[2-(5-methyl-2-imidazoline-2-yl)propane] dihydrochloride, 2,2'-azobisisobutylamide dihydrate, 2,2'-azobisisobutyronitrile, ammonium persulfate, potassium persulfate, benzoyl peroxide, diisopropylperoxy dicarbonate, t-butylperoxy 2-ethylhexanoate, t-butylperoxy pivalate, t-butylperoxy isobutylate, lauroyl peroxide, azobisisobutyronitril, 2,2'-azobis(2,4-dimethylvaleronitrile), t-butylperoxy neodecanoate, mixtures thereof, and the like. In particular, in case of homopolymerization of MPC or copolymerization of MPC with other monomer such as BMA having a vinyl group, 2,2'-azobisisobutyronitrile (abbreviated hereinafter as AIBN) is preferably used as a polymerization initiator in the light of polymerizability.

There is no specific limitation to an amount of a polymerization initiator, and for 100 parts by weight of all monomers used in polymerization, 0.01 to 10 parts by weight is preferable, and 0.1 to 5 parts by weight is more preferable. Moreover, polymerization is preferably carried out at 30 to 80.degree. C., more preferably at 40 to 70.degree. C. for 2 to 72 hours. In polymerization, a solvent can be used for effective polymerization reaction. Examples of the solvent include water, methanol, ethanol, propanol, t-butanol, benzene, toluene, dimethyl formamide, tetrahydrofuran, chloroform, a mixtures thereof, and the like. In particular, in case of homopolymerization of MPC or copolymerization of MPC with other monomer having a vinyl group, water and ethanol are preferably used in the light of solubility and polymerizability. Purification of the obtained polymers can be carried out by general method for purification such as reprecipitation, dialysis and ultrafiltration.

As a percentage of PC group in a polymer comprising a PC group, 1 to 100 mol % is preferable, and 5 to 10 mol % is more preferable per polymer comprising a PC group. Use of the polymer comprising less than 1 mol % of a PC group is not preferable because of difficulty in prevention of non-specific adsorption. In addition, average molecular weight of a polymer comprising a PC group varies depending on polymerization temperature, amount of polymerization initiator, whether a polymerization regulating agent is used or not, and the like. A polymer with a molecular weight (Mn) of 100 to 1,000,000 is preferable, and 1,000 to 500,000 is particularly preferable. There is no specific limitation to concentration of a compound having a PC group in the present invention, and concentration of 0.0001 to 10% is preferable, concentration of 0.001 to 5% is more preferable, and concentration of 0.01 to 1% is particularly preferable. Concentration less than 0.0001% is not preferable because reproducibility in determination does not improve remarkably. Concentration more than 10% is not also preferable because of incorrect determination ascribed to bubbles formed by terrible bubbling. Additionally, there is no specific limitation to a compound having a PC group, but homopolymer of MPC or copolymer of MPC with BMA is preferable.

In the present invention, agglutination immunoassay refers to an agglutination immunoassay which comprises allowing an antigenic substance in a sample to bind to insoluble carrier particles carrying substantially neither antigens nor antibodies thereon, and allowing an antibody or an antibody complex which reacts specifically to the antigenic substance to bind to the antigenic substance to give a selective agglutination of the insoluble carrier particles. However, in case an antibody or an antibody complex used in the present invention has an effect on values to be determined by reacting not only to the antigenic substance bound to insoluble carrier particles but also to the antigenic substance not bound to insoluble carrier particles, the following methods could be used as an agglutination immunoassay: a method wherein an antigenic substance in a sample is bound to insoluble carrier particles, and the free antigenic substance is removed by rinsing the insoluble carrier particles; a method of increasing the degrees of the antigenic substance bound to insoluble carrier particles to the free antigenic substance; a method of using the antibody or antibody complex which reacts to the antigenic substance bound to insoluble carrier particles, but does not substantially react to the free antigenic substance in the liquid phase.

In the present invention, insoluble carrier particles are generally used as a so-called latex suspension, wherein insoluble carrier particles such as latex are suspended in an aqueous medium such as a buffer solution. As a buffer for preparation of the buffer solution, a Good's buffer in addition to phosphoric acid buffer, carbonic acid buffer, and organic acid buffer can be used. As an acid for adjusting the pH of a buffer solution containing the buffer, an organic acid such as acetic acid as well as an inorganic acid such as hydrochloric acid, sulfuric acid and nitric acid can be used. In addition, as an alkali for adjusting the pH, sodium hydroxide, potassium hydroxide, lithium hydroxide, ammonium hydroxide and the like can be used. Moreover, in the present invention, surfactants effective for solubilization of lipid in a sample can also be used. In particular, a nonionic surfactant having a polyoxyethyleneglycol group, a cationic surfactant and an anionic surfactant can be used, if necessary.

As an antigenic substance in a sample which is a target to be determined in the agglutination immunoassay of the present invention, a substance capable of binding to insoluble carrier particles or a substance by which a corresponding polyclonal antibody or a monoclonal antibody can be obtained or prepared is preferable. However, in the light of facility to prepare the polyclonal antibody or monoclonal antibody, a substance such as protein with the molecular weight of 10,000 or more and glycoprotein with the molecular weight of 10,000 or more is more preferable as an antigenic substance. As an antigenic substance in a sample, Hemoglobin A1c (hereinafter abbreviated as HbA1c) in a blood sample is preferably exemplified. Moreover, as an antibody specifically bound to an antigenic substance in the present invention, a polyclonal antibody and/or a monoclonal antibody can be used. A monoclonal antibody can be obtained by cell fusion method reported by Koehler & Milstein (Nature, 256, 495–497, 1975). Additionally, as an antibody corresponding to the aforementioned HbA1c, an anti-HbA1c monoclonal antibody can be exemplified.

Meanwhile, it is well known that among monoclonal antibodies which are produced by hybridoma cells and selected by ELISA method, there are some monoclonal antibodies that do not react in an assay such as an radio immunoassay (RIA), wherein a reaction of an antigen with an antibody is carried out in a liquid phase. However, in the agglutination immunoassay according to the present invention, use of such monoclonal antibodies is preferable because reaction of the antibodies with the free antigenic substance in the liquid phase is inhibited to give a specific reaction of the antibodies with the antigenic substance bound to insoluble carrier particles.

In an agglutination immunoassay according to the present invention, there is a possibility that formation of an agglutination may not proceed by reacting the insoluble carrier particles carrying an antigenic substance, formed by binding an antigenic substance to insoluble carrier particles such as latex, with the monoclonal antibody. In such case, however, an agglutination can be brought about by using the antibody complex. That is, formation in advance of the antibody complex by reaction of the monoclonal antibody with the second antibody which reacts selectively to the monoclonal antibody, followed by reaction of the antibody complex with the antigenic substance bound to insoluble carrier particles such as latex can bring about an agglutination of the insoluble carrier particles. In addition to the above-mentioned method, an antibody complex can be formed by the following methods: addition of avidin to a biotin-labelled antibody; chemical bond by which an antibody is bound to an enzyme to give an enzyme-labelled antibody.

According to the present invention which enables a selective agglutination of insoluble carrier particles by reaction of an antigenic substance bound to insoluble carrier particles with an antibody or an antibody complex which reacts specifically to the antigenic substance, a reagent for an immunoassay can be prepared simply and easily, and a reagent for an immunoassay kept highly stable during storage can be supplied. That is, as the insoluble carrier particles such as latex do not carry neither antigens nor antibodies thereon, commercially available insoluble carrier particles carrying neither antigens nor antibodies thereon can be used as such. Furthermore, the antibodies used may not necessarily be the purified antibodies. Thus, the reagent is so simple that the reagent can be kept stable during storage.

Further, as an aqueous medium used in an agglutination immunoassay which comprises allowing an antigenic substance in a sample to bind to insoluble carrier particles carrying substantially neither antigens nor antibodies thereon, and allowing an antibody or an antibody complex which reacts specifically to the antigenic substance to bind to the antigenic substance in an aqueous medium comprising a compound having a group represented by formula (I) such as phophorylcholine to give an agglutination of the insoluble carrier particles to be measured, an aqueous medium in which non-specific adsorption and binding of the antibody or the antibody complex to the insoluble carrier particles such as latex can be prevented is preferred. Examples of the aqueous medium in which non-specific adsorption and binding of the antibody or the antibody complex to the insoluble carrier particles can be prevented include an aqueous solution comprising about 0.1 to 0.3% surfactant such as Tween 20, and the like.

There is no specific limitation to a vessel used in an agglutination reaction of the present invention, and a vessel of a tubular form such as a polystyrene test tube generally used in this type of agglutination reaction is exemplified. Moreover, in the light of easiness of batch treatment of many samples, a plate for ELISA having many wells (such as 96-well plate for ELISA "NUNC-IMMUNO PLATE", Nalge Nunc International K.K.) can be used. Additionally, in the light of easiness of an optical determination of agglutination of insoluble carrier particles such as latex, a reaction in a transparent vessel is preferable. In addition, in case of determining an agglutination of insoluble carrier particles such as latex by an autoanalyzer, agglutination reaction is usually carried out in a reaction vessel for the autoanalyzer.

There is no specific limitation to a method of measuring the degrees of an agglutination of insoluble carrier particles agglutination. In case of measuring an agglutination qualitatively or semiquantitatively, for example, degrees of agglutination of insoluble carrier particles can be determined visually, by comparing degrees of turbidity in measurement of agglutination of insoluble carrier particles using samples with the known concentration of the antigenic substances. In this measurement, for example, the less agglutination is formed, the more transparent the reaction mixture is. On the other hand, in case of measuring an agglutination quantitatively, for example, an optical measurement of agglutination is preferable in the light of easiness of measurement. As a method for an optical measurement of agglutination of insoluble carrier particles such as latex, the known methods for an optical measurement can be used. Examples include various methods such as nephelometry wherein formation of an agglutination is correlated to an increase of turbidity; a method of measuring a distribution of particles size wherein formation of an agglutination is correlated to a change in a distribution of particle size or an average diameter of particles; an integrating sphere turbidimetric assay wherein formation of an agglutination is correlated to a ratio of intensity of scattering light measured with an integrating sphere to intensity of transmitted light. A rate assay or an end-point assay can be applied to each of these methods for measurement. In the rate assay, degrees of agglutination are determined by an agglutination reaction rate, which is calculated on the basis of the differences of values to be measured at least two different points of the reaction. In the end-point assay, degrees of agglutination are determined by the values to be determined at a specific point, a point usually considered to be an end-point of the reaction. In the light of easiness and rapidness of measurement, a rate assay using nephelometry is preferable.

In the optical measurement of an agglutination of insoluble carrier particles such as latex with an average diameter of 0.04 to 0.8 μm, measurement by using a light with a wavelength of about 400 to 1400 nm is preferable.

As a reagent for an immunoassay according to the present invention, there is no specific limitation to a composition of the reagent as long as the reagent comprises a reagent for a measurement of an antigenic substance to be determined and a compound having a group represented by formula (I) such as a phoshorylchlorine group. Examples include a reagent kit comprising insoluble carrier particles, buffer, antibodies that bind to an antigen in a sample, and a compound having a group represented by formula (I), and the reagent kit may, if necessary, comprise surfactant, antiseptic, antibodies that bind to the antibodies to the antigen in a sample, and the like. In particular, a specific example of a reagent kit includes a reagent kit comprising a first reagent and a second reagent: a first reagent comprising insoluble carrier particles and buffer; and a second reagent comprising a compound having a group represented by formula (I) and antibodies that bind to the antigen. The first reagent and the second reagent in the reagent kit may further comprise, if necessary, surfactant, antiseptic, antibody that binds to the antigen in the sample, antibodies that bind to the antigen in a sample, antibodies for formation of an antibody complex that bind to the antibodies to the antigen in a sample, and the like.

EXAMPLES

The present invention will be described further in detail by the following Examples, Comparative Examples and Reference Examples, while the technical scope of the present invention will not be limited to these examples and the like.

Example 1

Reagents of the following composition were prepared.

| [Reagent R1] | |
|---|---|
| HEPES buffer (manufactured by DOJINDO Laboratories, pH 7.8) | 4.77 g/L |
| Latex particles (particle diameter: 0.0775 μm, manufactured by SEKISUI Chemical Co. Ltd.) | 0.033% by weight/L |
| NaN$_3$ (manufactured by Kanto Chemical Co., Inc.) | 0.1 g/L |
| [Reagent R2] | |
| HEPES buffer (manufactured by DOJINDO Laboratories, pH 7.0) | 4.77 g/L |
| Sodium chloride (manufactured by Wako Pure Chemical Industries, Ltd.) | 15 g/L |
| Polymer 2 (prepared in Reference Example 2) | 2 g/L |
| NaN$_3$ (manufactured by Kanto Chemical Co., Inc.) | 0.1 g/L |
| Anti-human HbA1c mouse monoclonal antibody (preparation in Preparation Example 1) | 0.025 g (in terms of IgG)/L |
| Anti-mouse IgG goat polyclonal antibody (manufactured by Wako Pure Chemical Industries, Ltd.) | 0.025 g (in terms of IgG)/L |

Example 2

Reagents of the following composition were prepared.

[Reagent R1]

| | |
|---|---|
| HEPES buffer (manufactured by DOJINDO Laboratories, pH 7.8) | 4.77 g/L |
| Latex particles (particle diameter: 0.0775 μm, manufactured by SEKISUI Chemical Co. Ltd.) | 0.033% by weight/L |
| NaN$_3$ (manufactured by Kanto Chemical Co., Inc.) | 0.1 g/L |

[Reagent R2]

| | |
|---|---|
| HEPES buffer (manufactured by DOJINDO Laboratories, pH 7.0) | 4.77 g/L |
| Sodium chloride (manufactured by Wako Pure Chemical Industries, Ltd.) | 15 g/L |
| Polymer 3 (prepared in Reference Example 3) | 2 g/L |
| NaN$_3$ (manufactured by Kanto Chemical Co., Inc.) | 0.1 g/L |
| Anti-human HbA1c mouse monoclonal antibody | 0.025 g (in terms of IgG)/L |
| Anti-mouse IgG goat polyclonal antibody (manufactured by Wako Pure Chemical Industries, Ltd.) | 0.025 g (in terms of IgG)/L |

Comparative Example 1

Reagents of the following composition comprising Tween 20 instead of polymer 2 in Example 1 or polymer 3 in Example 2 were prepared.

[Reagent R1]

| | |
|---|---|
| HEPES buffer (manufactured by DOJINDO Laboratories, pH 7.8) | 4.77 g/L |
| Latex particles (particle diameter: 0.0775 μm, manufactured by SEKISUI Chemical Co. Ltd.) | 0.033% by weight/L |
| NaN$_3$ (manufactured by Kanto Chemical Co., Inc.) | 0.1 g/L |

[Reagent R2]

| | |
|---|---|
| HEPES buffer (manufactured by DOJINDO Laboratories, pH 7.0) | 4.77 g/L |
| Sodium chloride (manufactured by Wako Pure Chemical Industries, Ltd.) | 15 g/L |
| Tween 20 (manufactured by Wako Pure Chemical Industries, Ltd.) | 2 g/L |
| NaN$_3$ (manufactured by Kanto Chemical Co., Inc.) | 0.1 g/L |
| Anti-human HbA1c mouse monoclonal antibody | 0.025 g (in terms of IgG)/L |

Anti-mouse IgG goat polyclonal antibody (manufactured by Wako Pure Chemical Industries, Ltd.) 0.025 g (in terms of IgG)/L

Comparative Example 2

Reagents of the following composition comprising Brij 30 instead of polymer 2 in Example 1 or polymer 3 in Example 2 were prepared.

[Reagent R1]

| | |
|---|---|
| HEPES buffer (manufactured by DOJINDO Laboratories, pH 7.8) | 4.77 g/L |
| Latex particles (particle diameter: 0.0775 μm, manufactured by SEKISUI Chemical Co. Ltd.) | 0.033% by weight/L |
| NaN$_3$ (Kanto Chemical Co., Inc.) | 0.1 g/L |

[Reagent R2]

| | |
|---|---|
| HEPES buffer (manufactured by DOJINDO Laboratories, pH 7.0) | 4.77 g/L |
| Sodium chloride (manufactured by Wako Pure Chemical Industries, Ltd.) | 15 g/L |
| Brij 30 (manufactured by Sigma) | 2 g/L |
| NaN$_3$ (manufactured by Kanto Chemical Co., Inc.) | 0.1 g/L |
| Anti-human HbA1c mouse monoclonal antibody | 0.025 g (in terms of IgG)/L |

Anti-mouse IgG goat polyclonal antibody (manufactured by Wako Pure Chemical Industries, Ltd.) 0.025 g (in terms of IgG)/L

Comparative Example 3

Reagents of the following composition comprising Brij 56 instead of polymer 2 in Example 1 or polymer 3 in Example 2 were prepared.

[Reagent R1]

| | |
|---|---|
| HEPES buffer (manufactured by DOJINDO Laboratories, pH 7.8) | 4.77 g/L |
| Latex particles (particle diameter: 0.0775 μm, manufactured by SEKISUI Chemical Co. Ltd.) | 0.033% by weight/L |
| NaN$_3$ (manufactured by Kanto Chemical Co., Inc.) | 0.1 g/L |

[Reagent R2]

| | |
|---|---|
| HEPES buffer (manufactured by DOJINDO Laboratories, pH 7.0) | 4.77 g/L |
| Sodium chloride (manufactured by Wako Pure Chemical Industries, Ltd.) | 15 g/L |
| Brij 56 (manufactured by Sigma) | 2 g/L |
| NaN$_3$ (manufactured by Kanto Chemical Co., Inc.) | 0.1 g/L |
| Anti-human HbA1c mouse monoclonal antibody | 0.025 g (in terms of IgG)/L |
| Anti-mouse IgG goat polyclonal antibody (manufactured by Wako Pure Chemical Industries, Ltd.) | 0.025 g (in terms of IgG)/L |

Example 3

Human blood was collected by EDTA blood collecting tube (VENOJECT Glass Vacuum Tubes; TERUMO Corp.) and left to stand for two hours. The prepicitated hemocyte layer (10 μL) was taken and the hemocyte layer was diluted with purified water (1 mL). The diluted hemocyte layer was frozen and stored at −20.degree. C., and the frozen hemocyte layer was melted just before use to give a sample. Determination of the concentration of HbA1c was carried out by using Reagent R1 and Reagent R2 prepared in Example 1, Example 2, Comparative Example 1, Comparative Example 2 and Comparative Example 3, respectively. Further, the calibration curve was diagramed by using the reagent just after unsealing, along with each of standard samples with HbA1c values of 0.0%, 4.2%, 7.7%, 11.3%, 14.8%, which were determined by glycohemoglobin autoanalyzer HLC-723 GHbV (Tosoh Corporation) using the reagent just after unsealing. Determination of HbA1c in the sample was carried out as follows. The sample (8 μL) prepared as above was added to Reagent R1 (240 μL), and the reaction was allowed to proceed at 37.degree. C. for 5 minutes. Then, Reagent R2 (80 μL) was added thereto, and the reaction was allowed to proceed at 37.degree. C. for 5 minutes. The change in absorbance was measured by the 2 point-end method (photometric points: 16–34) by Hitachi autoanalyzer 7170 at the main-wavelength of 450 nm and the sub-wavelength of 800 nm. Finally, the change in absorbance was correlated to the concentration of HbA1c in the sample on the diagram. This operation was repeated ten times to determine the average, the standard deviation and the within-run reproducibility [(the standard deviation×100)/the average)]. The results are shown in Table 1. As shown in Table 1, in comparison with Comparative Examples 1 to 3, degrees of agglutination were almost constant to give improved reproducibility in Examples 1 and 2.

TABLE 1

| Number of times of determination | Example 1 | Example 2 | Comparative Example 1 | Comparative Example 2 | Comparative Example 3 |
|---|---|---|---|---|---|
| 1 | 6.3 | 6.3 | 6.3 | 6.3 | 6.5 |
| 2 | 6.4 | 6.3 | 6.4 | 6.4 | 6.4 |
| 3 | 6.3 | 6.3 | 6.3 | 6.3 | 6.1 |
| 4 | 6.3 | 6.3 | 6.4 | 6.2 | 6.3 |
| 5 | 6.3 | 6.3 | 6.3 | 6.6 | 6.2 |
| 6 | 6.4 | 6.4 | 6.5 | 6.5 | 6.4 |
| 7 | 6.3 | 6.3 | 6.2 | 6.2 | 6.5 |
| 8 | 6.3 | 6.3 | 6.2 | 6.2 | 6.3 |
| 9 | 6.3 | 6.3 | 6.3 | 6.3 | 6.4 |
| 10 | 6.3 | 6.3 | 6.4 | 6.2 | 6.4 |
| average | 6.3 | 6.3 | 6.3 | 6.3 | 6.4 |
| standard deviation | 0.040 | 0.030 | 0.090 | 0.133 | 0.120 |
| within-run reproducibility | 0.63% | 0.48% | 1.42% | 2.10% | 1.90% |

Example 4

Reagents of the following composition were prepared.

[Reagent R1]

| | |
|---|---|
| HEPES buffer (manufactured by DOJINDO Laboratories, pH 7.8) | 4.77 g/L |
| Latex particles (particle diameter: 0.0775 μm, manufactured by SEKISUI Chemical Co. Ltd.) | 0.033% by weight/L |
| NaN$_3$ (manufactured by Kanto Chemical Co., Inc.) | 0.1 g/L |

| -continued | |
|---|---|
| Polymer 4 (prepared in Reference Example 4) | 1 g/L |
| [Reagent R2] | |
| HEPES buffer (manufactured by DOJINDO Laboratories, pH 7.0) | 4.77 g/L |
| Sodium chloride (manufactured by Wako Pure Chemical Industries, Ltd.) | 15 g/L |
| Tween 20 (manufactured by Wako Pure Chemical Industries, Ltd.) | 2 g/L |
| $NaN_3$ (manufactured by Kanto Chemical Co., Inc.) | 0.1 g/L |
| Anti-human HbA1c mouse monoclonal antibody | 0.025 g (in terms of IgG)/L |
| Anti-mouse IgG goat polyclonal antibody (manufactured by Wako Pure Chemical Industries, Ltd.) | 0.025 g (in terms of IgG)/L |

Example 5

Reagents of the following composition were prepared.

| [Reagent R1] | |
|---|---|
| HEPES buffer (manufactured by DOJINDO Laboratories, pH 7.8) | 4.77 g/L |
| Latex particles (particle diameter: 0.0775 μm, manufactured by SEKISUI Chemical Co. Ltd.) | 0.033% by weight/L |
| $NaN_3$ (manufactured by Kanto Chemical Co., Inc.) | 0.1 g/L |
| Polymer 5 (prepared in Reference Example 5) | 1 g/L |
| [Reagent R2] | |
| HEPES buffer (manufactured by DOJINDO Laboratories, pH 7.0) | 4.77 g/L |
| Sodium chloride (manufactured by Wako Pure Chemical Industries, Ltd.) | 15 g/L |
| Tween 20 (manufactured by Wako Pure Chemical Industries, Ltd.) | 2 g/L |
| $NaN_3$ (manufactured by Kanto Chemical Co., Inc.) | 0.1 g/L |
| Anti-human HbA1c mouse monoclonal antibody | 0.025 g (in terms of IgG)/L |
| Anti-mouse IgG goat polyclonal antibody (manufactured by Wako Pure Chemical Industries, Ltd.) | 0.025 g (in terms of IgG)/L |

Example 6

Reagents of the following composition were prepared.

| [Reagent R1] | |
|---|---|
| HEPES buffer (manufactured by DOJINDO Laboratories, pH 7.8) | 4.77 g/L |
| Latex particles (particle diameter: 0.0775 μm, manufactured by SEKISUI Chemical Co. Ltd.) | 0.033% by weight/L |
| $NaN_3$ (manufactured by Kanto Chemical Co., Inc.) | 0.1 g/L |
| Polymer 1 (prepared in Comparative Example 1) | 0.002 g/L |
| [Reagent R2] | |
| HEPES buffer (manufactured by DOJINDO Laboratories, pH 7.0) | 4.77 g/L |
| Sodium chloride (manufactured by Wako Pure Chemical Industries, Ltd.) | 15 g/L |
| Tween 20 (manufactured by Wako Pure Chemical Industries, Ltd.) | 2 g/L |
| $NaN_3$ (manufactured by Kanto Chemical Co., Inc.) | 0.1 g/L |
| Anti-human HbA1c mouse monoclonal antibody | 0.025 g (in terms of IgG)/L |
| Anti-mouse IgG goat polyclonal antibody (manufactured by Wako Pure Chemical Industries, Ltd.) | 0.025 g (in terms of IgG)/L |

Comparative Example 4

Reagents of the following composition which do not comprise polymer 4 in Example 4, polymer 5 in Example 5 and polymer 1 in Example 6 were prepared.

| [Reagent R1] | |
|---|---|
| HEPES buffer (manufactured by DOJINDO Laboratories, pH 7.8) | 4.77 g/L |
| Latex particles (particle diameter: 0.0775 μm, manufactured by SEKISUI Chemical Co. Ltd.) | 0.033% by weight/L |
| $NaN_3$ (manufactured by Kanto Chemical Co., Inc.) | 0.1 g/L |

-continued

[Reagent R2]

| | |
|---|---|
| HEPES buffer (manufactured by DOJINDO Laboratories, pH 7.0) | 4.77 g/L |
| Sodium chloride (manufactured by Wako Pure Chemical Industries, Ltd.) | 15 g/L |
| Tween 20 (manufactured by Wako Pure Chemical Industries, Ltd.) | 2 g/L |
| NaN$_3$ (manufactured by Kanto Chemical Co., Inc.) | 0.1 g/L |
| Anti-human HbA1c mouse monoclonal antibody | 0.025 g (in terms of IgG)/L |
| Anti-mouse IgG goat polyclonal antibody (manufactured by Wako Pure Chemical Industries, Ltd.) | 0.025 g (in terms of IgG)/L |

Example 7

Human blood was collected by EDTA blood collecting tube (VENOJECT Glass Vacuum Tubes; TERUMO Corp.) and left to stand for two hours. The prepicitated hemocyte layer (10 μL) was taken and the hemocyte layer was diluted with purified water (1 mL). The diluted hemocyte layer was frozen and stored at −20.degree. C., and the frozen hemocyte layer was melted just before use to give a sample. Determination of the concentration of HbA1c was carried out in the same manner as in Example 3, by using the sample along with Reagent R1 and Reagent R2 prepared in Examples 4 to 6, and Comparative Example 4, respectively. The results are shown in Table 2. As shown in Table 2, in Examples 4 to 6, degrees of agglutination were almost constant to give improved reproducibility in comparison with Comparative Example 4.

TABLE 2

| Number of times of determination | Example 4 | Example 5 | Example 6 | Comparative Example 4 |
|---|---|---|---|---|
| 1 | 6.3 | 6.3 | 6.3 | 6.5 |
| 2 | 6.3 | 6.3 | 6.4 | 6.3 |

TABLE 2-continued

| Number of times of determination | Example 4 | Example 5 | Example 6 | Comparative Example 4 |
|---|---|---|---|---|
| 3 | 6.3 | 6.2 | 6.2 | 6.3 |
| 4 | 6.3 | 6.3 | 6.3 | 6.1 |
| 5 | 6.3 | 6.3 | 6.2 | 6.2 |
| 6 | 6.3 | 6.2 | 6.3 | 6.4 |
| 7 | 6.3 | 6.3 | 6.3 | 6.3 |
| 8 | 6.3 | 6.3 | 6.3 | 6.4 |
| 9 | 6.2 | 6.3 | 6.3 | 6.3 |
| 10 | 6.3 | 6.3 | 6.3 | 6.2 |
| average | 6.3 | 6.3 | 6.3 | 6.3 |
| standard deviation | 0.030 | 0.040 | 0.054 | 0.110 |
| within-run reproducibility | 0.48% | 0.64% | 0.86% | 1.74% |

Example 8

Reagents of the following composition were prepared.

[Preparation of R1 solution (latex)]

| | |
|---|---|
| HEPES buffer (manufactured by DOJINDO Laboratories, pH 7.8) | 4.77 g/L |
| Latex (particle diameter: 0.0775 μm, manufactured by SEKISUI Chemical Co. Ltd.) | 0.033% by weight/L |
| NaN$_3$ (manufactured by Kanto Chemical Co., Inc.) | 0.1 g/L |
| Polymer 4 (prepared in Reference Example 4) | 2 g/L |

[Preparation of R2 (antibody) solution]

| | |
|---|---|
| HEPES buffer (manufactured by DOJINDO Laboratories, pH 7.0) | 4.77 g/L |
| Sodium chloride (manufactured by Wako Pure Chemical Industries, Ltd.) | 15 g/L |
| Tween 20 (manufactured by Wako Pure Chemical Industries, Ltd.) | 2 g/L |
| NaN$_3$ (manufactured by Kanto Chemical Co., Inc.) | 0.1 g/L |
| Anti-human HbA1c mouse monoclonal antibody | 0.025 g (in terms of IgG)/L |
| Anti-mouse IgG goat polyclonal antibody (manufactured by Wako Pure Chemical Industries, Ltd.) | 0.025 g (in terms of TgG)/L |

Example 9

Reagents of the following composition were prepared.

| [Reagent R1] | |
|---|---|
| HEPES buffer (manufactured by DOJINDO Laboratories, pH 7.8) | 4.77 g/L |
| Latex (particle diameter: 0.0775 μm, manufactured by SEKISUI Chemical Co. Ltd.) | 0.033% by weight/L |
| NaN$_3$ (manufactured by Kanto Chemical Co., Inc.) | 0.1 g/L |
| Polymer 4 (prepared in Reference Example 4) | 5 g/L |
| [Reagent R2] | |
| HEPES buffer (manufactured by DOJINDO Laboratories, pH 7.0) | 4.77 g/L |
| Sodium chloride (manufactured by Wako Pure Chemical Industries, Ltd.) | 15 g/L |
| Tween 20 (manufactured by Wako Pure Chemical Industries, Ltd.) | 2 g/L |
| NaN$_3$ (manufactured by Kanto Chemical Co., Inc.) | 0.1 g/L |
| Anti-human HbA1c mouse monoclonal antibody | 0.025 g (in terms of IgG)/L |
| Anti-mouse IgG goat polyclonal antibody (manufactured by Wako Pure Chemical Industries, Ltd.) | 0.025 g (in terms of IgG)/L |

Example 10

Human blood was collected by EDTA blood collecting tube (VENOJECT Glass Vacuum Tubes; TERUMO Corp.) and left to stand for two hours. The prepicitated hemocyte layer (10 μL) was taken, and the hemocyte layer was made to 1 mL with purified water to give a sample 1. Further, human blood was collected by EDTA blood collecting tube (VENOJECT Glass Vacuum Tubes; TERUMO Corp.) and left to stand for two hours. A supernatant (4 μL) and a prepicitated hemocyte layer (10 μL) were taken, and the supernatant and the prepicitated hemocyte layer were made to 1 mL with purified water to give a sample 2. Determination of the concentration of HbA1c in the samples was carried out in the same manner as in Example 3 by using these samples along with Reagent R1 and Reagent R2 prepared in Example 4, Example 8, Example 9 and Comparative Example 4, respectively. Averages in three times of determinations for each sample are shown in Table 3. As shown in Table 3, in Example 4, Example 8 and Example 9, particularly, in Examples 8 and 9 with higher content of polymer 4, the degrees of agglutination were almost constant to give improved reproducibility even in the determination using the sample 2 comprising plasma, in comparison with Comparative Example 4.

TABLE 3

| Reagent | Sample 1 | Sample 2 |
|---|---|---|
| Example 4 | 6.6 | 6.1 |
| Example 8 | 6.7 | 6.5 |
| Example 9 | 6.7 | 6.7 |
| Comparative Example 4 | 6.6 | 5.1 |

Reference Example 1

(Preparation of Polymer 1)

MPC (NOF Corporation) (35.7 g) and BMA (Wako Pure Chemical Industries, Inc. )(4.3 g), dissolved in ethanol (160 g), were put into a four-neck flask, and nitrogen gas was bubbled into the ethanol solution for 30 minutes. After heating the ethanol solution to 60. degree. C., polymerization initiator AIBN (Wako Pure Chemical Industries, Inc.) (0.82 g) was added thereto, and the polymerization reaction was allowed to proceed for 8 hours. With stirring the solution after the polymerization reaction, the solution was added dropwise to diethyl ether (3 L). The formed precipitate was filtered, and dried in vacuo at room temperature for 48 hours to give the copolymer (polymer 1) as a powder with the ratio of MPC (0.8 mol) to BMA (0.2 mol). Molecular weight of this polymer 1 was evaluated 153,000 as a weight-average molecular weight, by gel permeation chromatography (abbreviated hereinafter as GPC) analysis. The GPC analysis was carried out under the following condition: eluent: phosphate buffer (pH 7.4, 20 mM); standard: polyethyleneglycol; detection: UV (210 nm) and refractive index (this condition in GPC analysis was also used in References 2 to 5).

Reference Example 2

(Preparation of polymer 2)

MPC (20.3 g) and BMA (9.75 g), dissolved in ethanol (120 g), were put into a four-neck flask, and nitrogen gas was bubbled into the ethanol solution for 30 minutes. After heating the ethanol solution to 60.degree. C., AIBN (0.35 g) was added thereto, and the polymerization reaction was allowed to proceed for 8 hours. With stirring the solution after the polymerization reaction, the solution was added dropwise to diethyl ether (3 L). The formed precipitate was filtered, and dried in vacuo at room temperature for 48 hours to give the copolymer (polymer 2) as a powder with the ratio of MPC (0.5 mol) to BMA (0.5 mol). Molecular weight of this polymer 2 was evaluated 224,000 as a weight-average molecular weight, by GPC analysis.

Reference Example 3

(Preparation of polymer 3)

MPC (14.1 g) and BMA (15.9 g), dissolved in ethanol (120 g), were put into a four-neck flask, and nitrogen gas was bubbled into the ethanol solution for 30 minutes. After heating the ethanol solution to 60.degree. C., AIBN (0.35 g) was added thereto, and the polymerization reaction was allowed to proceed for 8 hours. With stirring the solution after the polymerization reaction, the solution was added dropwise to diethyl ether (3 L). The formed precipitate was filtered, and dried in vacuo at room temperature for 48 hours to give the copolymer (polymer 3) as a powder with the ratio of MPC (0.3 mol) to BMA (0.7 mol). Molecular weight of this polymer 3 was evaluated 130,000 as a weight-average molecular weight, by GPC analysis.

Reference Example 4

(Preparation of polymer 4)

MPC (50.0 g), dissolved in ethanol (160 g), was put into a four-neck flask, and nitrogen gas was bubbled into the ethanol solution for 30 minutes. After heating the ethanol solution to 60.degree. C., AIBN (0.24 g) was added thereto, and the polymerization reaction was allowed to proceed for 8 hours. With stirring the solution after the polymerization reaction, the solution was added dropwise to diethyl ether (3 L). The formed precipitate was filtered, and dried in vacuo at room temperature for 48 hours to give the homopolymer of MPC (polymer 4) as a powder. Molecular weight of this polymer 4 was evaluated 529,000 as a weight-average molecular weight, by GPC analysis.

Reference Example 5

(Preparation of polymer 5)

MPC (30.0 g), dissolved in ethanol (120 g), was put into a four-neck flask, and nitrogen gas was bubbled into the ethanol solution for 30 minutes. After heating the ethanol solution to 60.degree. C., AIBN (0.48 g) was added thereto, and the polymerization reaction was allowed to proceed for 8 hours. With stirring the solution after the polymerization reaction, the solution was added dropwise to diethyl ether (3 L). The formed precipitate was filtered, and dried in vacuo at room temperature for 48 hours to give the homopolymer of MPC (polymer 5) as a powder. Molecular weight of this polymer 5 was evaluated 183,000 as a weight-average molecular weight, by GPC analysis. Reference Example 6 (Preparation of the monoclonal antibody to the glycopeptide epitope of the N terminus of the β chain in hemoglobin A1c)

According to the description of the Preparation Example 1 in Japanese Published Unexamined Patent Application No. 35752/95, the peptide of Val-His-Leu-Thr-Pro-Cys, corresponding to the amino acid sequence of the N terminus of the β chain in hemoglobin, was prepared, and glucose was allowed to bind non-enzymatically to the a-amino group of Val, the amino acid residue of the N terminus to give the glycopeptide. Further, the glycopeptide was allowed to bind to the carrier protein through a spacer to give the immunogen. The monoclonal antibody that reacts to HbA1c but does not react to HbA0 was obtained by conventional method. The obtained monoclonal antibody was an antibody which does not react to free HbA1c, but reacts to HbA1 bound to insoluble carrier particles.

INDUSTRIAL APPLICABILITY

According to the present invention wherein a compound having a group represented by formula (I) such as a phosphorylcholine group is used, a stable and uniform reaction of immunological agglutination using insoluble carrier particles such as latex proceeds to give a determination with good reproducibility.

The invention claimed is:

1. An agglutination immunoassay for determining the presence and/or amount of an antigenic substance in a sample, which comprises allowing an antigenic substance in a sample to bind to insoluble carrier particles carrying substantially neither antigens nor antibodies thereon, and allowing an antibody or an antibody complex which reacts specifically to the antigenic substance to bind to the antigenic substance to give a selective agglutination of the insoluble carrier particles in the presence of a compound having a group represented by formula (I),

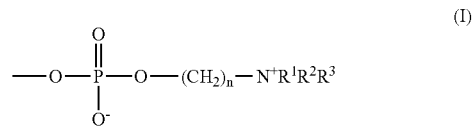

wherein n is an integer of 1 to 6, and $R^1$, $R^2$ and $R^3$ are the same or different, and independently represent hydrogen, substituted or unsubstituted alkyl having 1 to 6 carbon atoms, and measuring the degree of selective agglutination of the insoluble carrier particles, which indicates the presence and/or amount of antigenic substance in the sample.

2. The agglutination immunoassay according to claim 1, wherein the compound having a group represented by formula (I) is a compound prepared by polymerization of a monomer having a group represented by formula (I).

3. The agglutination immunoassay according to claim 1, wherein the compound having a group represented by formula (I) is a compound prepared by polymerization of a monomer having a group represented by formula (I) with other monomer polymerizable with the monomer having a group represented by formula (I).

4. The agglutination immunoassay according to claim 3, wherein the other monomer polymerizable with the monomer having a group represented by formula (I) is a monomer having a vinyl group.

5. The agglutination immunoassay according to claim 4, wherein the monomer having a vinyl group is n-butyl methacrylate.

6. The agglutination immunoassay according to claim 2, wherein the monomer having a group represented by formula (I) is a monomer having a group represented by formula (I) and a vinyl group.

7. The agglutination immunoassay according to claim 1, wherein the group represented by formula (I) is a phosphorylcholine group.

8. The agglutination immunoassay according to claim 6, wherein the monomer having a group represented by formula (I) and a vinyl group is 2-methacryloyloxyethyl phosphorylcholine.

9. The agglutination immunoassay according to claim 1, wherein the antibody is an anti-hemoglobin A1c monoclonal antibody.

10. The agglutination immunoassay according to claim 1, wherein the antibody complex comprises an antibody which reacts specifically to the antigenic substance, and a secondary antibody which reacts selectively to the antibody which reacts specifically to the antigenic substance.

11. The agglutination immunoassay according to claim 1, wherein the insoluble carrier particles are polystyrene latex.

12. A reagent kit for an immunoassay comprising an insoluble carrier particle carrying substantially neither antigens nor antibodies thereon, an antibody that binds to an antigen to be determined in a sample, and a compound having a group represented by formula (I),

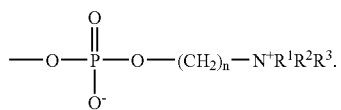

wherein n is an integer of 1 to 6, and $R^1$, $R^2$ and $R^3$ are the same or different, and independently represent hydrogen, substituted or unsubstituted alkyl having 1 to 6 carbon atoms.

13. The reagent kit for an immunoassay according to claim 12, wherein the compound having a group represented by formula (1) is a compound prepared by polymerization of a monomer having a group represented by formula (I).

14. The reagent kit for an immunoassay according to claim 12, wherein the compound having a group represented by formula (D is a compound prepared by polymerization of a monomer having a group represented by formula (I) with other monomer polymerizable with the monomer having a group represented by formula (I).

15. The reagent kit for an immunoassay according to claim 14, wherein the other monomer polymerizable with the monomer having a group represented by formula (I) is a monomer having a vinyl group.

16. The reagent kit for an immunoassay according to claim 15, wherein the monomer having a vinyl group is n-butyl methacrylate.

17. The reagent kit for an immunoassay according to claim 13, wherein the monomer having a group represented by formula (I) is a monomer having a group represented by formula (I) and a vinyl group.

18. The reagent kit for an immunoassay according to claim 12, wherein the group represented by formula (I) is a phosphorylcholine group.

19. The reagent kit for an immunoassay according to claim 17, wherein the monomer having a group represented by formula (I) and a vinyl group is 2-methacryloyloxyehtyl phosphorylcholine.

20. The reagent kit for an immunoassay according to claim 12, wherein the antibody is an anti-hemoglobin A1c monoclonal antibody.

21. The reagent kit for an immunoassay according to claim 12, wherein the insoluble carrier particles are polystyrene latex.

22. The reagent kit for an immunoassay according to claim 12, further comprising a secondary antibody that binds to the antibody that binds to the antigen to be determined in the sample.

23. The reagent kit for an immunoassay according to claim 12, further comprising a buffer.

* * * * *